United States Patent
Akagane (10) Patent No.: US 12,121,257 B2
(45) Date of Patent: Oct. 22, 2024

(54) ULTRASOUND TRANSDUCER, ULTRASOUND TREATMENT TOOL, AND MANUFACTURING METHOD OF ULTRASOUND TRANSDUCER

(71) Applicant: OLYMPUS CORPORATION, Hachioji (JP)

(72) Inventor: Tsunetaka Akagane, Hachioji-shi (JP)

(73) Assignee: OLYMPUS CORPORATION, Tokyo (JP)

( * ) Notice: Subject to any disclaimer, the term of this patent is extended or adjusted under 35 U.S.C. 154(b) by 912 days.

(21) Appl. No.: 17/185,613

(22) Filed: Feb. 25, 2021

(65) Prior Publication Data

US 2021/0177453 A1  Jun. 17, 2021

Related U.S. Application Data

(63) Continuation of application No. PCT/JP2018/032216, filed on Aug. 30, 2018.

(51) Int. Cl.
*A61B 17/32* (2006.01)
*B06B 1/06* (2006.01)
*A61B 17/00* (2006.01)

(52) U.S. Cl.
CPC .... *A61B 17/320092* (2013.01); *B06B 1/0614* (2013.01); *A61B 2017/00402* (2013.01);
(Continued)

(58) Field of Classification Search
CPC .. A61B 17/320092; A61B 2017/00402; A61B 2017/00526; A61B 2017/320082;
(Continued)

(56) References Cited

U.S. PATENT DOCUMENTS

2001/0041880 A1  11/2001  Brisken et al.
2012/0025652 A1   2/2012  Nakamura et al.
(Continued)

FOREIGN PATENT DOCUMENTS

JP  H02-86874 A   3/1990
JP  H9-155288 A   6/1997
(Continued)

OTHER PUBLICATIONS

Nov. 20, 2018 International Search Report issued in International Application No. PCT/JP2018/032216.

*Primary Examiner* — Ryan J. Severson
(74) *Attorney, Agent, or Firm* — Oliff PLC (57) ABSTRACT

An ultrasound transducer includes a transducer body configured to generate ultrasound vibration to vibrate a treatment portion that treats a living tissue. The transducer body includes a plurality of piezoelectric elements configured to alternately repeat expansion and contraction according to a supplied drive signal. The plurality of piezoelectric elements are integrally fastened in a state where the plurality of piezoelectric elements are stacked along a direction of expansion and contraction. The plurality of piezoelectric elements include a first piezoelectric element configured to expand at a first timing and contract at a second timing, and a second piezoelectric element whose expansion and contraction timings are different from expansion and contraction timings of the first piezoelectric element. The second piezoelectric element is arranged so that a polarization direction of the second piezoelectric element is a same as a polarization direction of an adjacent piezoelectric element.

20 Claims, 6 Drawing Sheets

(52) U.S. Cl.
CPC ............... *A61B 2017/00526* (2013.01); *A61B 2017/320082* (2017.08); *A61B 2017/320095* (2017.08); *B06B 2201/55* (2013.01); *B06B 2201/76* (2013.01)

(58) Field of Classification Search
CPC ....... A61B 2017/320089; A61B 2017/320095; B06B 1/0614; B06B 2201/55; B06B 2201/76
See application file for complete search history.

(56) References Cited

U.S. PATENT DOCUMENTS

| | | |
|---|---|---|
| 2012/0256521 A1 | 10/2012 | Nishikubo |
| 2012/0293044 A1 | 11/2012 | Bromfield |
| 2015/0088154 A1 | 3/2015 | Vaitekunas et al. |
| 2018/0297079 A1 | 10/2018 | Toda |

FOREIGN PATENT DOCUMENTS

| | | |
|---|---|---|
| JP | 2001-179179 A | 7/2001 |
| JP | 2002-533152 A | 10/2002 |
| JP | 6261833 B2 | 1/2018 |
| WO | 2016/046887 A1 | 3/2016 |
| WO | 2017/109917 A1 | 6/2017 |

ULTRASOUND TRANSDUCER, ULTRASOUND TREATMENT TOOL, AND MANUFACTURING METHOD OF ULTRASOUND TRANSDUCER

CROSS-REFERENCE TO RELATED APPLICATION

This application is a continuation of International Application No. PCT/JP2018/032216, filed on Aug. 30, 2018, the entire contents of which are incorporated herein by reference.

BACKGROUND

1. Technical Field

The present disclosure relates to an ultrasound transducer, an ultrasound treatment tool, and a manufacturing method of an ultrasound transducer.

2. Related Art

In the relater art, an ultrasound treatment tool that includes an ultrasound transducer generating ultrasound vibration according to a supplied drive signal and that treats a living tissue by applying the ultrasound vibration to the living tissue is known (see, for example, Japanese Patent No. 6261833).

The ultrasound transducer disclosed in Japanese Patent No. 6261833 includes a plurality of piezoelectric elements that are stacked and integrated by a bolt penetrating along a stacking direction of the plurality of piezoelectric elements and that alternately repeat expansion and contraction along the stacking direction according to a drive signal. That is, the ultrasound transducer includes a bolt-tightened Langevin type transducer (BLT).

SUMMARY

In some embodiments, an ultrasound transducer includes a transducer body configured to generate ultrasound vibration to vibrate a treatment portion that treats a living tissue, the transducer body including a plurality of piezoelectric elements configured to alternately repeat expansion and contraction according to a supplied drive signal, the plurality of piezoelectric elements being integrally fastened in a state where the plurality of piezoelectric elements are stacked along a direction of expansion and contraction, the plurality of piezoelectric elements including a first piezoelectric element configured to expand at a first timing and contract at a second timing, and a second piezoelectric element whose expansion and contraction timings are different from expansion and contraction timings of the first piezoelectric element, the second piezoelectric element being arranged so that a polarization direction of the second piezoelectric element is a same as a polarization direction of an adjacent piezoelectric element.

In some embodiments, an ultrasound treatment tool includes a treatment portion configured to treat a living tissue and an ultrasound transducer including a transducer body configured to generate ultrasound vibration to vibrate the treatment portion, the transducer body including a plurality of piezoelectric elements configured to alternately repeat expansion and contraction according to a supplied drive signal, the plurality of piezoelectric elements being integrally fastened in a state where the plurality of piezoelectric elements are stacked along a direction of expansion and contraction, the plurality of piezoelectric elements including a first piezoelectric element configured to expand at a first timing and contract at a second timing, and a second piezoelectric element whose expansion and contraction timings are different from expansion and contraction timings of the first piezoelectric element, the second piezoelectric element being arranged so that a polarization direction of the second piezoelectric element is a same as a polarization direction of an adjacent piezoelectric element.

In some embodiments, provided is a manufacturing method of an ultrasound transducer. The ultrasound transducer includes a plurality of piezoelectric elements configured to alternately repeat expansion and contraction according to a supplied drive signal, the plurality of piezoelectric elements being fastened integrally in a state where the plurality of piezoelectric elements are stacked along an expansion and contraction direction, the ultrasound transducer being configured to generate ultrasound vibration by expansion and contraction of the plurality of piezoelectric elements in constant current control. The manufacturing method includes measuring amplitude of the ultrasound transducer in a state of arrangement in a posture in which polarization directions of the plurality of piezoelectric elements are inverted for each piezoelectric element with respect to a normal state of arrangement in a posture in which the polarization directions of the plurality of piezoelectric elements are along a specific direction, and determining a piezoelectric element whose polarization direction is to be inverted, based on the amplitude, from among the plurality of piezoelectric elements.

The above and other features, advantages and technical and industrial significance of this disclosure will be better understood by reading the following detailed description of presently preferred embodiments of the disclosure, when considered in connection with the accompanying drawings.

DETAILED DESCRIPTION

Schematic Configuration of Treatment System

Figure 1:
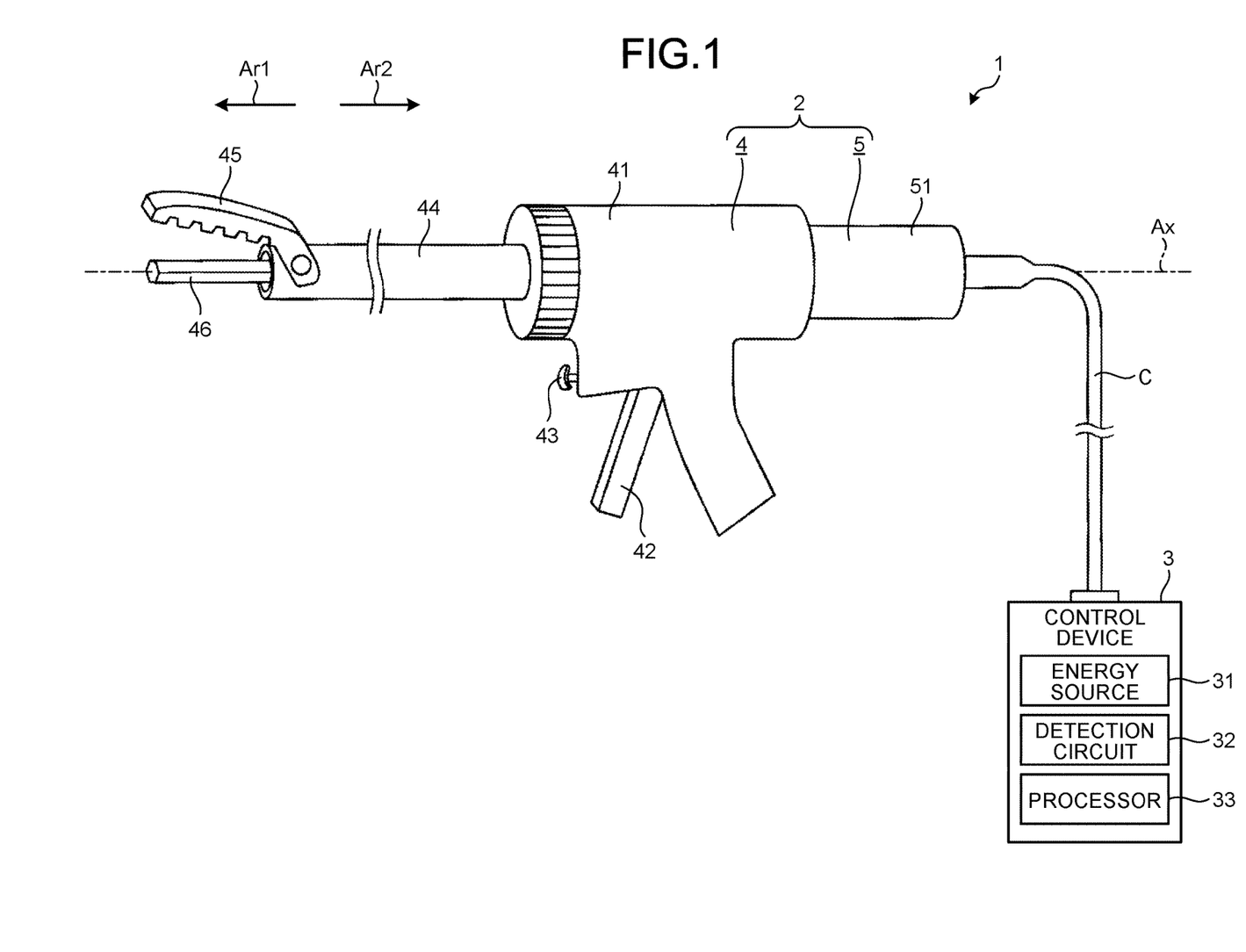
FIG. 1 is a diagram illustrating a treatment system according to an embodiment.

FIG. 1 is a diagram illustrating a schematic configuration of a treatment system 1 according to the present embodiment.

The treatment system 1 treats a site to be treated (hereinafter, referred to as a target site) in a living tissue by applying ultrasound energy to the target site. Here, the treatment means, for example, coagulation and incision of a target site. As illustrated in FIG. 1, the treatment system 1 includes an ultrasound treatment tool 2 and a control device 3.

Configuration of Ultrasound Treatment Tool

The ultrasound treatment tool 2 is, for example, a medical treatment tool that treats a target site while passing through the abdominal wall. As illustrated in FIG. 1, the ultrasound treatment tool 2 includes a handpiece 4 and an ultrasound transducer 5.

As illustrated in FIG. 1, the handpiece 4 includes a holding case 41, an operation knob 42, a switch 43, a sheath 44, a jaw 45, and an ultrasound probe 46.

The holding case 41 supports the entire ultrasound treatment tool 2.

The operation knob 42 is movably attached to the holding case 41 and accepts opening/closing operation by a surgeon.

The switch 43 is provided in a state of being exposed to the outside of the holding case 41, and accepts output start operation by a surgeon. Then, the switch 43 outputs an operation signal corresponding to the output start operation to the control device 3.

The sheath 44 has a cylindrical shape. Hereinafter, the central axis of the sheath 44 is referred to as a central axis Ax (FIG. 1). Hereinafter, one side along the central axis Ax is referred to as a distal end side Ar1 (FIG. 1), and the other side will be referred to as a proximal end side Ar2 (FIG. 1). A part of the proximal end side Ar2 is inserted from the distal end side Ar1 of the holding case 41 to the inside of the holding case 41, so that the sheath 44 is attached to the holding case 41.

The jaw 45 is rotatably attached to the end of the distal end side Ar1 of the sheath 44 and grips the target site in between the jaw 45 and a portion of the distal end side Ar1 of the ultrasound probe 46. The inside of the holding case 41 and the sheath 44 described above is provided with an opening/closing mechanism (not shown) that opens/closes the jaw 45 with respect to the portion of the distal end side Ar1 of the ultrasound probe 46 in response to an opening/closing operation of the operation knob 42 by a surgeon.

The ultrasound probe 46 corresponds to a treatment portion according to the disclosure. This ultrasound probe 46 has a long shape extending linearly along the central axis Ax, and as illustrated in FIG. 1, is inserted to the inside of the sheath 44 in a state where a portion of the distal end side Ar1 projecting outward. The end of the proximal end side Ar2 of the ultrasound probe 46 is connected to an ultrasound transducer 6 (see (a) of FIG. 2) included in the ultrasound transducer 5. Then, the ultrasound probe 46 transmits the ultrasound vibration generated by the ultrasound transducer 6 from the end of the proximal end side Ar2 to the end of the distal end side Ar1.

Figure 2:
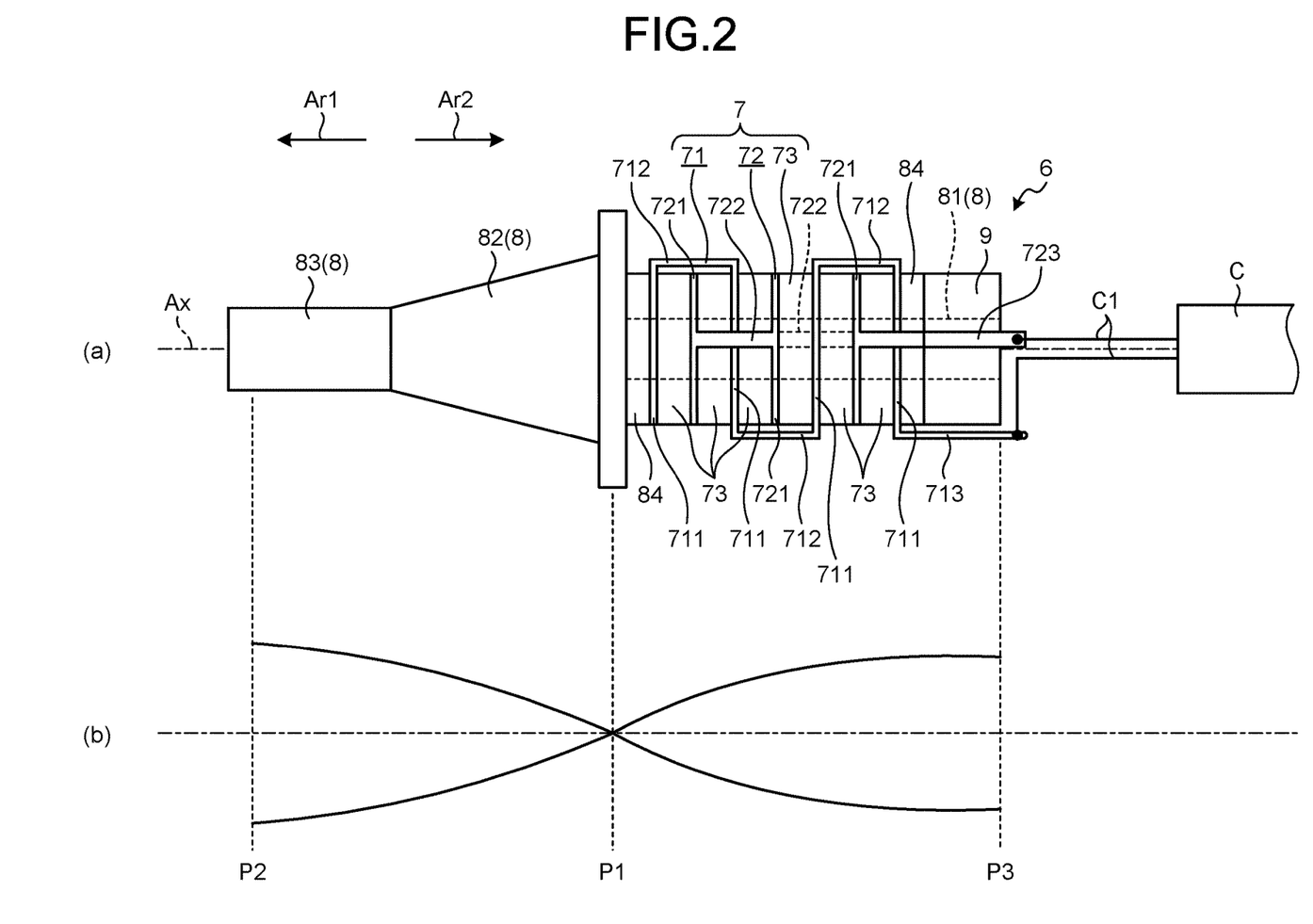
FIG. 2 is a diagram illustrating an ultrasound transducer.

As illustrated in FIG. 1, the ultrasound transducer 5 includes an ultrasound transducer case 51 and the ultrasound transducer 6 (see (a) of FIG. 2).

The ultrasound transducer case 51 supports the ultrasound transducer 6 and is attachably and detachably connected to the holding case 41.

FIG. 2 is a diagram illustrating the ultrasound transducer 6.

The ultrasound transducer 6 generates ultrasound vibration under the control of the control device 3. In the present embodiment, the ultrasound transducer 6 includes a bolt-tightened Langevin type transducer (BLT). As illustrated in (a) of FIG. 2, the ultrasound transducer 6 includes a transducer body 7, a front mass 8, and a back mass 9.

As illustrated in (a) of FIG. 2, the transducer body 7 includes first and second electrode plates 71, 72, and a plurality of (six in the present embodiment) piezoelectric elements 73.

Figure 3:
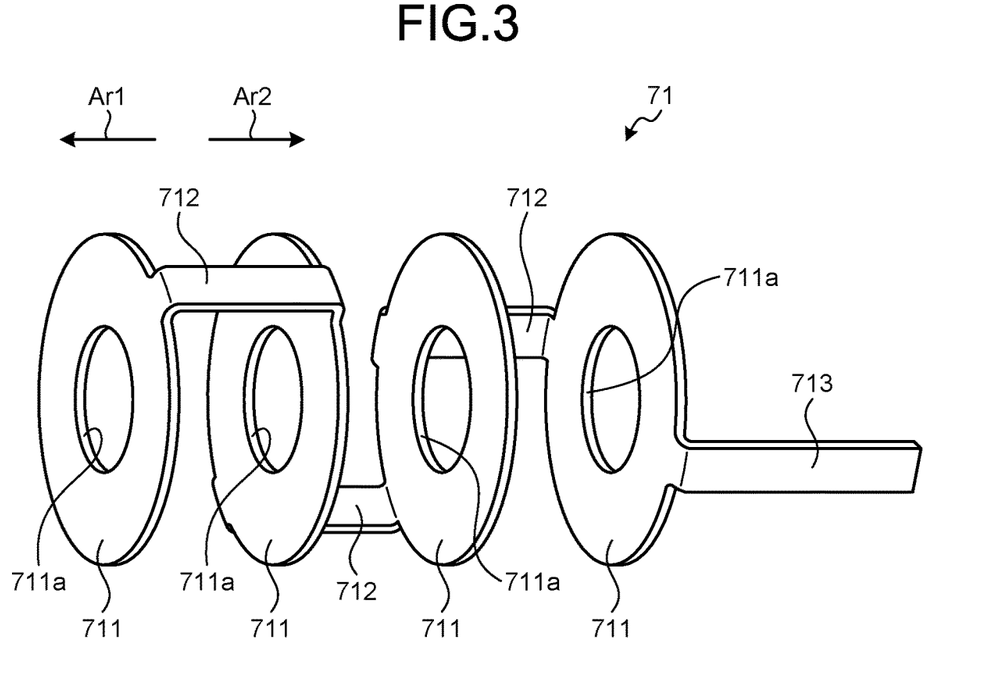
FIG. 3 is a diagram illustrating a first electrode plate.

FIG. 3 is a diagram illustrating the first electrode plate 71.

The first electrode plate 71 is a portion to which a drive signal is supplied from the control device 3. As illustrated in (a) of FIG. 2 or FIG. 3, the first electrode plate 71 includes a plurality of (four in the present embodiment) negative electrode plates 711 and a plurality of (three in the present embodiment) negative electrode wiring portions 712, and a lead wire connection terminal 713.

As illustrated in FIG. 3, the plurality of negative electrode plates 711 each have a disk shape having an aperture 711a in the center, and are arrayed side by side along the central axis Ax.

The plurality of negative electrode wiring portions 712 are portions in which the outer edges of the negative electrode plates 711 adjacent to each other are electrically connect to each other.

The lead wire connection terminal 713 is a portion to which a lead wire C1 ((a) of FIG. 2) included in an electric cable C (FIG. 1 and (a) of FIG. 2) is connected. The lead wire connection terminal 713 extends from the outer edge of the negative electrode plate 711 located at the most proximal end side Ar2 among the plurality of negative electrode plates 711 to the proximal end side Ar2.

Figure 4:
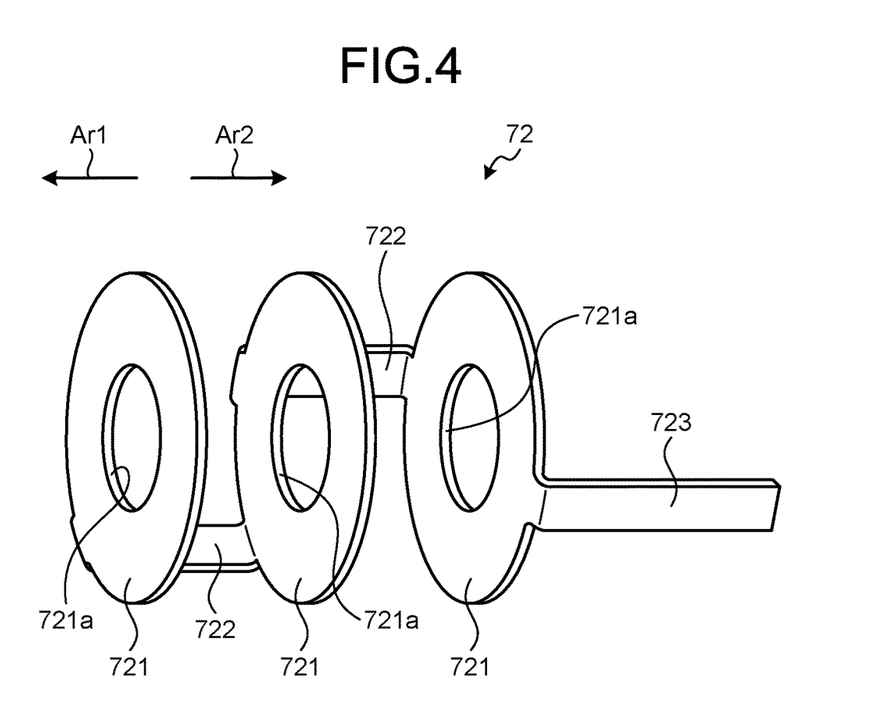
FIG. 4 is a diagram illustrating a second electrode plate.

FIG. 4 is a diagram illustrating the second electrode plate 72.

The second electrode plate 72 is a portion to which a drive signal is supplied from the control device 3. As illustrated in (a) of FIG. 2 or FIG. 4, the second electrode plate 72 includes a plurality of (three in the present embodiment) positive electrode plates 721, a plurality of (two in the present embodiment) positive electrode wiring portions 722, and a lead wire connection terminal 723.

As illustrated in FIG. 4, the plurality of positive electrode plates 721 each have a disk shape having an aperture 721a in the center, and are arrayed side by side along the central axis Ax. The positive electrode plate 721 has substantially the same shape as the negative electrode plate 711.

The plurality of positive electrode wiring portions 722 are portions in which the outer edges of the positive electrode plates 721 adjacent to each other are electrically connected to each other.

The negative electrode plates 711 and the positive electrode plates 721 are alternately arranged along the central axis Ax as illustrated in (a) of FIG. 2.

The lead wire connection terminal 723 is a portion to which the lead wire C1 included in the electric cable C is connected. The lead wire connection terminal 723 extends from the outer edge of the positive electrode plate 721 located at the most proximal end side Ar2 among the plurality of positive electrode plates 721 to the proximal end side Ar2.

Each of the plurality of piezoelectric elements 73 has a disk shape having an aperture (not shown) in the center, and is arranged between the negative electrode plate 711 and the positive electrode plate 721. That is, the plurality of piezoelectric elements 73 are stacked along the central axis Ax. Then, a potential difference is generated in the stacking direction along the central axis Ax in response to the drive signals supplied to the first and second electrode plates 71, 72, so that the plurality of piezoelectric elements 73 alternately repeat expansion and contraction along the stacking direction. As a result, the ultrasound transducer 6 generates ultrasound vibration of longitudinal vibration whose vibration direction is the stacking direction.

The front mass 8 has an elongated shape extending linearly along the central axis Ax. As illustrated in (a) of FIG. 2, the front mass 8 includes an element mounting portion 81, a cross-sectional area changing portion 82, and a probe mounting portion 83.

The element mounting portion 81 is a bolt extending linearly along the central axis Ax, and the element mounting portions 81 are inserted to each aperture 711*a* of the plurality of negative electrode plates 711, each aperture 721*a* of the plurality of positive electrode plates 721, and each aperture (not shown) of the plurality of piezoelectric elements 73. As illustrated in (a) of FIG. 2, the back mass 9 formed of a nut is attached to an end of the element mounting portion 81 on the proximal end side Ar2.

The cross-sectional area changing portion 82 corresponds to a horn according to the disclosure. The cross-sectional area changing portion 82 is provided at an end of the element mounting portion 81 on the distal end side Ar1, and is a portion in which the amplitude of ultrasound vibration is amplified. As illustrated in (a) of FIG. 2, the cross-sectional area changing portion 82 is set so that an end of the cross-sectional area changing portion 82 on the proximal end side Ar2 has a larger diameter than the element mounting portion 81, and the cross-sectional area changing portion 82 has a truncated cone shape in which the cross-sectional area of the cross-sectional area changing portion 82 decreases toward the distal end side Ar1. That is, the element mounting portion 81 penetrates the plurality of negative electrode plates 711, the plurality of positive electrode plates 721, and the plurality of piezoelectric elements 73 along the central axis Ax, and the plurality of negative electrode plates 711, the plurality of positive electrode plates 721, and the plurality of piezoelectric elements 73 are sandwiched between the cross-sectional area changing portion 82 and the back mass 9, so that the plurality of negative electrode plates 711, the plurality of positive electrode plates 721, and the plurality of piezoelectric elements 73 are integrally fastened in a state of having a substantially cylindrical shape. In the present embodiment, an insulating plate 84 ((a) of FIG. 2) is interposed between the cross-sectional area changing portion 82 and the piezoelectric element 73, and between the back mass 9 and the piezoelectric element 73.

As illustrated in (a) of FIG. 2, the probe mounting portion 83 is provided at an end of the cross-sectional area changing portion 82 on the distal end side Ar1, and extends linearly along the central axis Ax. An end of the ultrasound probe 46 on the proximal end side Ar2 is connected to an end of the probe mounting portion 83 on the distal end side Ar1 in a state where the ultrasound transducer 5 is connected to the handpiece 4.

Configuration of Control Device

The ultrasound treatment tool 2 is attachably and detachably connected to the control device 3 by the electric cable C (FIG. 1). The control device 3 comprehensively controls the operation of the ultrasound treatment tool 2 by passing through the electric cable C. As illustrated in FIG. 1, the control device 3 includes an energy source 31, a detection circuit 32, and a processor 33.

The energy source 31 outputs a drive signal, which is AC power, to the ultrasound transducer 6 via the electric cable C (a pair of lead wires C1) under the control of the processor 33.

The detection circuit 32 detects a US signal based on the drive signal output from the energy source 31 to the ultrasound transducer 6. Then, the detection circuit 32 outputs the detected US signal to the processor 33.

Here, examples of the US signal include a voltage phase signal in the drive signal (hereinafter, referred to as a US voltage phase signal), a current phase signal in the drive signal (hereinafter, referred to as a US current phase signal), a current value in the drive signal (hereinafter, referred to as a US current), a voltage value in the drive signal (hereinafter, referred to as US voltage), and an impedance value calculated from the US current and the US voltage (hereinafter, referred to as US impedance).

The processor 33 is, for example, a central processing unit (CPU) or a field-programmable gate array (FPGA), and controls the operation of the entire treatment system 1 according to a program stored in a memory (not shown).

The functions of the processor 33 will be described in the "Operation of treatment system" below.

Operation of Treatment System

Next, the operation of the treatment system 1 described above will be described.

A surgeon holds the ultrasound treatment tool 2 by hand and inserts a portion of the distal end side Ar1 of the ultrasound treatment tool 2 into the abdominal cavity after passing the portion through the abdominal wall using, for example, a trocca. Then, the surgeon performs aperture and closing operation of the operation knob 42, and grips the target site by the jaw 45 and the portion of the distal end side Ar1 of the ultrasound probe 46. Thereafter, the surgeon presses the switch 43. Then, the processor 33 executes the controls described below in response to the operation signal from the switch 43.

The processor 33 controls the operation of the energy source 31, sweeps the frequency in the drive signal output from the energy source 31, and searches for the resonance frequency of the ultrasound transducer 6 based on the US signal output from the detection circuit 32 (for example, the phase difference of the US current, the US current phase signal, and the US voltage phase signal). Then, the processor 33 controls the operation of the energy source 31, and performs PLL control of locking the frequency in the drive signal output from the energy source 31 to the resonance frequency that has been found by the search, based on the US signal (for example, the phase difference among the US current, the US current phase signal, and the US voltage phase signal). In the present embodiment, the processor 33 performs constant current control of keeping the US current constant when performing PLL control. As a result, the ultrasound transducer 6 generates ultrasound vibration (longitudinal vibration). Here, the end of the cross-sectional area changing portion 82 on the proximal end side Ar2 serves as a node P1 of longitudinal vibration ((b) of FIG. 2). The end of the probe mounting portion 83 on the distal end side Ar1 and the end of the back mass 9 on the proximal end side Ar2 are antinodes P2 and P3 ((b) of FIG. 2) of longitudinal vibration, respectively. That is, the total length of the ultrasound transducer 6 is about half the wavelength of longitudinal vibration.

Then, the longitudinal vibration generated in the ultrasound transducer 6 is transmitted to the ultrasound probe 46. As a result, a portion of the ultrasound probe 46 on the distal end side Ar1 vibrates with a desired amplitude due to the longitudinal vibration. That is, ultrasound vibration is applied to the target site gripped between the jaw 45 and the portion of the ultrasound probe 46 on the distal end side Ar1, from the portion of the distal end side Ar1. In other words, ultrasound energy is applied to the target site from the portion of the ultrasound probe 46 on the distal end side Ar1. As a result, frictional heat is generated between the portion of the distal end side Ar1 and the target site. Then, the target site is incised while coagulating.

Manufacturing Method of Ultrasound Transducer

Next, a manufacturing method of the ultrasound transducer 6 will be described.

Figure 5:
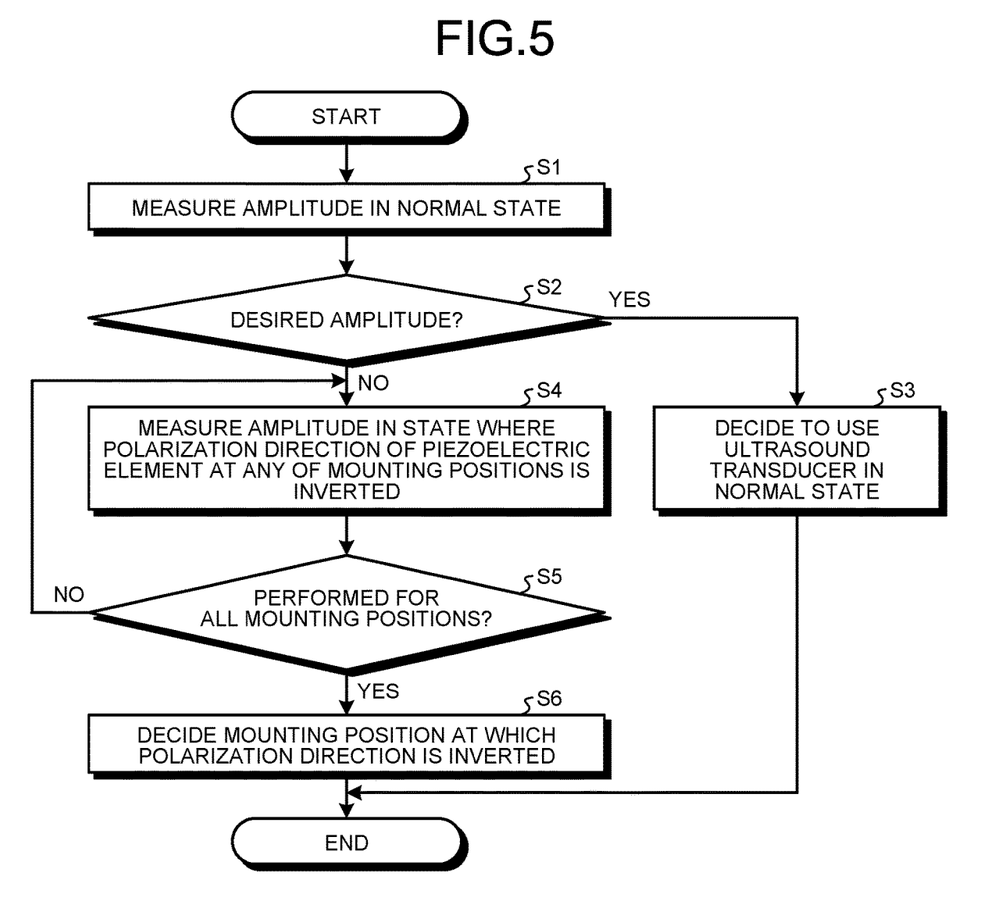
FIG. 5 is a flowchart illustrating a manufacturing method of an ultrasound transducer.
Figure 6A:
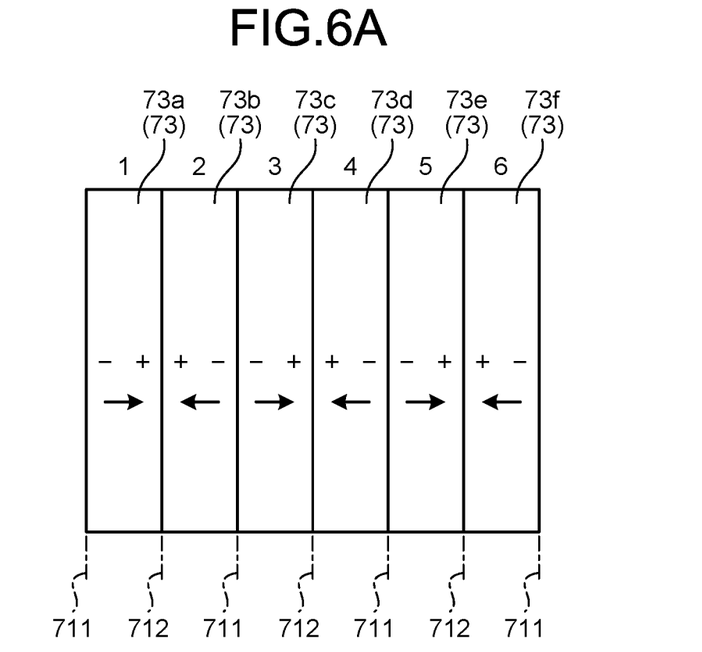
FIGS. 6A and 6B are diagrams for explaining a manufacturing method of an ultrasound transducer.
Figure 6B:
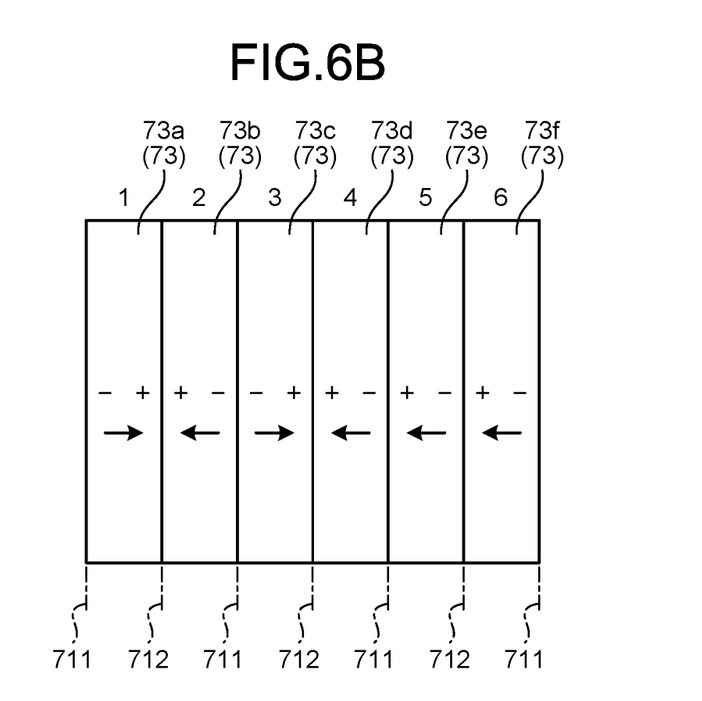
Figure 7:
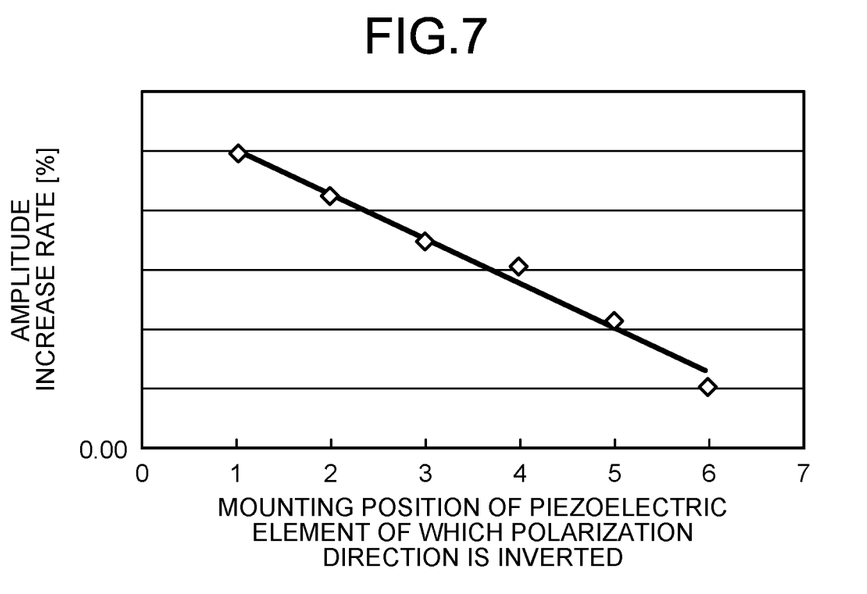
FIG. 7 is a diagram for explaining a manufacturing method of an ultrasound transducer.

FIG. 5 is a flowchart illustrating a manufacturing method of the ultrasound transducer 6. FIGS. 6A, 6B and 7 are diagrams for explaining a manufacturing method of the ultrasound transducer 6. Specifically, FIG. 6A illustrates a configuration in which a plurality of piezoelectric elements 73 are arranged in a normal state. FIG. 6B illustrates a configuration of arrangement in a posture in which the polarization direction of a piezoelectric element 73e of the plurality of piezoelectric elements 73 is reversed from the normal state.

In FIGS. 6A and 6B, the mounting positions of the plurality of piezoelectric elements 73 are set to the mounting positions "1" to "6" in order from the side close to the cross-sectional area changing portion 82 (node P1) toward the proximal end side Ar2. The piezoelectric elements 73 at the mounting positions "1" to "6" are the piezoelectric elements 73a to 73f, respectively. The positive charge inside the piezoelectric element 73 is represented by "+", the negative charge is represented by "−", and the polarization direction is represented by an arrow. The positions of the negative electrode plate 711 and the positive electrode plate 721 are represented by the alternate long and short dash line.

Here, the normal state illustrated in FIG. 6A means a state where the plurality of piezoelectric elements 73 are arranged in a posture in which the negative charge "−" side faces the negative electrode plate 711 and the positive charge "+" side faces the positive electrode plate 721.

First, an operator performs Step S1 described below.

The operator sets the plurality of piezoelectric elements 73 to the normal state illustrated in FIG. 6A. The operator operates the control device 3 and causes the control device 3 to perform constant current control of the ultrasound transducer 6. As a result, the ultrasound transducer 6 generates ultrasound vibration (longitudinal vibration). In this case, since the plurality of piezoelectric elements 73 are set to the normal state, the plurality of piezoelectric elements 73 expand at the same first timing and contract at the same second timing. Then, the operator measures the amplitude of the longitudinal vibration by using a vibrometer or the like.

After Step S1, the operator determines whether the amplitude measured in Step S1 is the desired amplitude (Step S2).

When it is determined that the amplitude is the desired amplitude (Step S2: Yes), the operator decides to use the ultrasound transducer 6 in the normal state (Step S3). After Step S3, the operator finishes the manufacturing method of the ultrasound transducer 6.

On the other hand, when it is determined that the amplitude is not the desired amplitude (Step S2: No), the operator performs Step S4 described below.

For example, as illustrated in FIG. 6B, the operator performs arrangement in a posture in which the polarization direction of one piezoelectric element 73 at any of the mounting positions "1" to "6" (the piezoelectric element 73e in the example of FIG. 6B) is inverted from the normal state. As similar to Step S1, the operator operates the control device 3 and causes the control device 3 to perform constant current control of the ultrasound transducer 6. As a result, the ultrasound transducer 6 generates ultrasound vibration (longitudinal vibration). In this case, for example, in the state of FIG. 6B, of the plurality of piezoelectric elements 73, the piezoelectric elements 73a to 73d, 73f expand at the same first timing and contract at the same second timing. That is, the piezoelectric elements 73a to 73d, 73f correspond to the first piezoelectric element according to the disclosure. On the other hand, since the polarization direction of the piezoelectric element 73e is inverted from the normal state, the piezoelectric element 73e contracts at the first timing and expands at the second timing, contrary to the piezoelectric elements 73a to 73d, 73f. That is, the piezoelectric element 73e corresponds to the second piezoelectric element according to the disclosure. Then, the operator measures the amplitude of the longitudinal vibration by using a vibrometer or the like.

After Step S4, the operator determines whether or not Step S4 has been performed for all the piezoelectric elements 73 at the mounting positions "1" to "6" (Step S5).

When it is determined that Step S4 has not been performed for all the piezoelectric elements 73 (Step S5: No), the operator returns the process to Step S4.

On the other hand, when it is determined that Step S4 has been performed for all the piezoelectric elements 73 (Step S5: Yes), the operator performs Step S6 described below.

The operator refers to the amplitude measured in Step S4, and decides a mounting position at which an amplitude close to a desired amplitude is obtained by inverting the polarization direction, from among the mounting positions "1" to "6". Then, the operator decides to use the ultrasound transducer 6 in a posture in which the polarization direction of the piezoelectric element 73 at the decided mounting position is inverted from the normal state. In the present embodiment, as illustrated in FIG. 6B, the mounting position "5" is decided as the mounting position for inverting the polarization direction.

The relationship between the increase rate of each amplitude measured in Step S4 with respect to the amplitude in the normal state measured in Step S1 (hereinafter, referred to as the amplitude increase rate) and mounting positions "1" to "6" of the piezoelectric element 73 of which polarization direction has been inverted is as illustrated in FIG. 7.

The amplitude increase rate is a positive value regardless of which of the polarization direction of any of the piezoelectric elements 73a to 73f at the mounting positions "1" to "6" is inverted from the normal state. In other words, the amplitude is higher than the amplitude in the normal state. The reasons as below can be considered for this.

When the polarization direction of any of the piezoelectric elements 73a to 73f is reversed from the normal state, the vibration efficiency of the ultrasound transducer 6 becomes worse than that in the normal state. When the vibration efficiency deteriorates, the voltage value applied to each of the piezoelectric elements 73a to 73f in the constant current control becomes higher than in the normal state. That is, when the polarization direction of any of the piezoelectric elements 73a to 73f is inverted from the normal state, the applied voltage value becomes higher than the normal state, so that the amplitude becomes higher than the amplitude in the normal state.

The amplitude increase rate is highest when the polarization direction of the piezoelectric element 73a at the mounting position "1" is inverted from the normal state, and the amplitude decreases as the mounting position of the piezoelectric element 73 at which the polarization direction is inverted changes from "2" to "6" (as the mounting position changes so as to be away from the node P1). The reasons as below can be considered for this.

Of the plurality of piezoelectric elements 73, the piezoelectric element 73a mounted at a position close to the node P1 has the highest vibration contribution rate that contributes to the vibration of the ultrasound transducer 6, and the vibration contribution rate is smaller in the order of the piezoelectric elements 73a to 73f mounted at the mounting positions "1" to "6". That is, when the polarization direction of the piezoelectric element 73 having a high vibration contribution rate is inverted from the normal state, the amplitude increase rate becomes high, and when the polarization direction of the piezoelectric element 73 having a low vibration contribution rate is inverted from the normal state, the amplitude increase rate becomes low.

According to the present embodiment described above, the effects as below are obtained.

In the ultrasound transducer 6 according to the present embodiment, the plurality of piezoelectric elements 73 includes the piezoelectric elements 73a to 73d, 73f that expand at the first timing and contract at the second timing, and the piezoelectric element 73e that contracts at the first timing and expands at the second timing. That is, a desired amplitude can be obtained only by inverting the polarization direction of the piezoelectric element 73e among the plurality of piezoelectric elements 73 from the normal state. At this time, even when the polarization direction of the piezoelectric element 73e is inverted from the normal state, the capacitance of the entire piezoelectric element 73 does not change from the capacitance of the entire piezoelectric element 73 in the normal state. Therefore, even when the polarization direction of the piezoelectric element 73e is inverted from the normal state, it is not necessary to change the control structure from the design manufacturing structure in order to control the ultrasound transducer 6. That is, there is no need to make major design changes.

From the above, according to the ultrasound transducer 6 according to the present embodiment, a desired amplitude can be easily obtained without making a significant design change.

In the ultrasound transducer 6 according to the present embodiment, the plurality of piezoelectric elements 73 are stacked along the central axis Ax at the proximal end side Ar2 relative to the node P1. In other words, the ultrasound transducer 6 has only one longitudinal vibration node P1, and its total length is about half the wavelength of the longitudinal vibration. Therefore, it is possible to reduce the size of the ultrasound transducer 6 and, further, the size of the ultrasound treatment tool 2.

Other Embodiments

The embodiment for carrying out the disclosure has been described, but the disclosure should not be limited only by the above-described embodiment.

In the above-described embodiment, the plurality of piezoelectric elements 73 include six elements, but may include elements of other numbers. Further, of the six piezoelectric elements 73, the fifth piezoelectric element 73e from the node P1 i used as the second piezoelectric element according to the disclosure, but the disclosure is not limited to this, and the piezoelectric element 73 at other positions may be used as the second piezoelectric element according to the disclosure. The number of the second piezoelectric elements according to the disclosure is not limited to one, and may be any other number.

In the above-described embodiment, the piezoelectric element 73e, which is the second piezoelectric element according to the disclosure contracts at the first timing and expands at the second timing, contrary to the piezoelectric elements 73a to 73d, 73f which are the first piezoelectric elements according to the disclosure. As the second piezoelectric element according to the disclosure, the expansion and contraction timings may be other timings as long as the expansion and contraction timings are different from those of the first piezoelectric element according to the disclosure. That is, if the timing of expansion and contraction of the second piezoelectric element according to the disclosure is different from that of the first piezoelectric element according to the disclosure, it is considered that the amplitude is higher than the amplitude in the normal state since the ultrasound transducer 6 has a worse vibration efficiency than that in the normal state.

In the above-described embodiment, the ultrasound transducer 6 has a total length of about half the wavelength of the ultrasound vibration, but the disclosure is not limited to this, and the ultrasound transducer 6 may have other total lengths, for example, a total length substantially the same as the wavelength.

In the above-described embodiment, the ultrasound treatment tool 2 employs a configuration in which ultrasound energy is applied to the target site, but the disclosure is not limited to this, and the ultrasound treatment tool 2 may employ a configuration in which ultrasound energy and at least one of high frequency and thermal energy is applied to the target site. Here, "applying high frequency energy to the target site" means passing a high-frequency current to the target site. Further, "applying heat energy to the target site" means transferring heat from a heater or the like to the target site.

According to an ultrasound transducer, an ultrasound treatment tool, and a manufacturing method of an ultrasound transducer according to the disclosure, a desired amplitude can be easily obtained.

Additional advantages and modifications will readily occur to those skilled in the art. Therefore, the disclosure in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An ultrasound transducer comprising
   a transducer body configured to generate ultrasound vibration,
   the transducer body including a plurality of piezoelectric elements configured to repeatedly alternate between expansion and contraction,
   the plurality of piezoelectric elements including:
   a first piezoelectric element having a first polarization direction; and
   a second piezoelectric element provided adjacent to the first piezoelectric element in a direction of expansion and contraction, the second piezoelectric element having a second polarization direction of the second piezoelectric element being the same direction as the first polarization direction of the first piezoelectric element.

2. The ultrasound transducer according to claim 1, wherein the first piezoelectric element is configured to expand at a first timing and contract at a second timing.

3. The ultrasound transducer according to claim 1, further comprising a horn connected to the transducer body, the horn being configured to:
   amplify the ultrasound vibration; and
   transmit the ultrasound vibration from the transducer body to a treatment portion.

4. The ultrasound transducer according to claim 1, wherein:
   the ultrasound vibration has a node and an antinode; and
   the second piezoelectric element is located closer to the antinode than the node.

5. The ultrasound transducer according to claim 1, the plurality of piezoelectric elements further comprising:
   a third piezoelectric element, a fourth piezoelectric element, a fifth piezoelectric element, and a sixth piezoelectric element, wherein:

each of the third piezoelectric element, the fourth piezoelectric element, the fifth piezoelectric element, and the sixth piezoelectric element are stacked along the direction of expansion and contraction, and the second piezoelectric element is arranged at a fifth position among the first piezoelectric element, the second piezoelectric element, the third piezoelectric element, the fourth piezoelectric element, the fifth piezoelectric element, and the sixth piezoelectric element from a distal side of the plurality of piezoelectric elements.

6. The ultrasound transducer according to claim 1, wherein
the transducer body is configured to generate the ultrasound vibration by constant current control.

7. The ultrasound transducer according to claim 1, further comprising at least one positive electrode and at least one negative electrode,
wherein:
the first piezoelectric element is arranged so that a positive charge inside the first piezoelectric element faces one of the at least one positive electrode and a negative charge inside the first piezoelectric element faces one of the at least one negative electrode, and
the second piezoelectric element is arranged so that one of: (1) a positive charge inside the second piezoelectric element faces the one of the at least one negative electrode; and (2) a negative charge in the inside of the second piezoelectric element faces the one of the at least one positive electrode.

8. An ultrasound treatment tool comprising:
the ultrasound transducer according to claim 1; and
a treatment portion configured to treat living tissue wherein the transducer body is configured to vibrate the treatment portion.

9. The ultrasound treatment tool according to claim 8, wherein the second piezoelectric element is configured to contract at the first timing and expand at the second timing.

10. The ultrasound treatment tool according to claim 8, the ultrasound transducer further comprising:
a horn connected to the transducer body, the horn being configured to:
amplify the ultrasound vibration; and
transmit the ultrasound vibration from the transducer body to a treatment portion.

11. The ultrasound treatment tool according to claim 10, wherein:
the ultrasound vibration has a node and an antinode;
the second piezoelectric element is located closer to the antinode than the node.

12. The ultrasound treatment tool according to claim 11, wherein:
the plurality of piezoelectric elements further include a third piezoelectric element, a fourth piezoelectric element, a fifth piezoelectric element, and a sixth piezoelectric element,
each of the third piezoelectric element, the fourth piezoelectric element, the fifth piezoelectric element, and the sixth piezoelectric element are stacked along the direction of expansion and contraction; and
the second piezoelectric element is arranged at a fifth position among the first piezoelectric element, the second piezoelectric element, the third piezoelectric element, the fourth piezoelectric element, the fifth piezoelectric element, and the sixth piezoelectric element from a distal side of the plurality of piezoelectric elements.

13. The ultrasound treatment tool according to claim 8, further comprising at least one positive electrode and at least one negative electrode, the at least one positive electrode and the at least one negative electrode being alternately arranged along a direction of expansion and contraction of the plurality of piezoelectric elements, wherein
the first piezoelectric element is arranged so that a positive charge in an inside of the first piezoelectric element faces one of the at least one positive electrode and a negative charge in the inside of the first piezoelectric element faces one of the at least one negative electrode, and
the second piezoelectric element is arranged so that one of: (1) a positive charge in an inside of the second piezoelectric element faces the one of the at least one negative electrode; and (2) a negative charge in the inside of the second piezoelectric element faces the one of the at least one positive electrode.

14. The ultrasound transducer according to claim 1, wherein:
the first piezoelectric element is configured to expand at a first timing and contract at a second timing, and
the second piezoelectric element is configured to expand at a third timing that is different from the first timing and contract at a fourth timing that is different from the second timing.

15. The ultrasound transducer according to claim 14, further comprising a processor is configured to:
determine a resonance frequency of the ultrasound transducer; and
cause an energy source to output a drive signal at the resonance frequency.

16. The ultrasound transducer according to claim 1, wherein
the transducer body is configured to generate the ultrasound vibration to vibrate a treatment portion configured to treat living tissue,
the plurality of piezoelectric elements is configured to repeatedly alternate between expansion and contraction according to a supplied drive signal, and
the plurality of piezoelectric elements are integrally fastened such that the plurality of piezoelectric elements are stacked along the a direction of expansion and contraction.

17. The ultrasound transducer according to claim 1, wherein:
the plurality of piezoelectric elements further include a third piezoelectric element,
the third piezoelectric element has a third polarization direction of the third piezoelectric element being the same direction as the first polarization direction, and
the third piezoelectric element is provided adjacent to the second piezoelectric element.

18. The ultrasound transducer according to claim 17, wherein:
the plurality of piezoelectric elements further include a fourth piezoelectric elements,
the fourth piezoelectric element has a fourth second polarization direction being opposite to the first polarization direction, and
the fourth piezoelectric element is provided adjacent to the first piezoelectric element.

19. The ultrasound transducer according to claim 1, wherein:
- the plurality of piezoelectric elements further include a third piezoelectric element, a fourth piezoelectric element, a fifth piezoelectric element, and a sixth piezoelectric element,
- each of the third piezoelectric element, the fourth piezoelectric element, the fifth piezoelectric element, and the sixth piezoelectric element are stacked along the direction of expansion and contraction,
- each of the first piezoelectric element, the third piezoelectric element, the fourth piezoelectric element, the fifth piezoelectric element and the sixth piezoelectric element are configured to expand at a first timing and contract at a second timing, and
- the second piezoelectric element is configured to expand at the second timing and contract at the first timing.

20. The ultrasound transducer according to claim 1, further comprising:
- a front mass provided distally relative to the plurality of piezoelectric elements; and
- a back mass provided proximally relative to the plurality of piezoelectric elements, wherein the second piezoelectric element is located closer to the back mass than the front mass.

* * * * *